US011324696B2

(12) United States Patent
Fallin et al.

(10) Patent No.: US 11,324,696 B2
(45) Date of Patent: May 10, 2022

(54) SUSPENSIONS AND DILUENTS FOR METRONIDAZOLE AND BACLOFEN

(71) Applicant: Azurity Pharmaceuticals, Inc., Woburn, MA (US)

(72) Inventors: Ken Fallin, Diamondhead, MS (US); Zeus Pendon, Woburn, MA (US); Priya Capila, Wellesley, MA (US); Neal Muni, Wellesley, MA (US)

(73) Assignee: AZURITY PHARMACEUTICALS, INC., Woburn, MA (US)

( * ) Notice: Subject to any disclaimer, the term of this patent is extended or adjusted under 35 U.S.C. 154(b) by 21 days.

(21) Appl. No.: 17/133,415

(22) Filed: Dec. 23, 2020

(65) Prior Publication Data

US 2021/0220267 A1 Jul. 22, 2021

Related U.S. Application Data

(63) Continuation of application No. 16/331,733, filed as application No. PCT/US2017/050714 on Sep. 8, 2017, now abandoned.

(60) Provisional application No. 62/385,325, filed on Sep. 9, 2016.

(51) Int. Cl.
| *A61K 9/10* | (2006.01) |
| *A61K 9/00* | (2006.01) |
| *A61K 31/197* | (2006.01) |
| *A61K 31/4164* | (2006.01) |
| *A61K 47/12* | (2006.01) |
| *A61K 47/26* | (2006.01) |
| *A61K 47/34* | (2017.01) |
| *A61K 47/36* | (2006.01) |
| *A61K 47/38* | (2006.01) |
| *A61K 47/46* | (2006.01) |
| *A61P 31/04* | (2006.01) |
| *A61P 33/02* | (2006.01) |

(52) U.S. Cl.
CPC .............. *A61K 9/10* (2013.01); *A61K 9/0095* (2013.01); *A61K 31/197* (2013.01); *A61K 31/4164* (2013.01); *A61K 47/12* (2013.01); *A61K 47/26* (2013.01); *A61K 47/34* (2013.01); *A61K 47/36* (2013.01); *A61K 47/38* (2013.01); *A61K 47/46* (2013.01); *A61P 31/04* (2018.01); *A61P 33/02* (2018.01); *Y02A 50/30* (2018.01)

(58) Field of Classification Search
None
See application file for complete search history.

(56) References Cited

U.S. PATENT DOCUMENTS

| 8,012,496 | B2 | 9/2011 | Dudhara et al. |
| 8,426,470 | B2 | 4/2013 | Dharmadhikari et al. |
| 8,969,414 | B2 | 3/2015 | Foster et al. |
| 9,180,108 | B2 | 11/2015 | Schmitz et al. |
| 9,254,268 | B2 | 2/2016 | Temtsin et al. |
| 9,289,408 | B2 | 3/2016 | Trissel et al. |
| 9,597,304 | B2 | 3/2017 | Schmitz et al. |
| 10,300,015 | B2 | 5/2019 | Cohen et al. |
| 2002/0165211 | A1 | 11/2002 | Biggadike et al. |
| 2005/0142271 | A1 | 6/2005 | Ojima et al. |
| 2006/0094787 | A1 | 5/2006 | Forenzo et al. |
| 2006/0127480 | A1 | 6/2006 | Tobyn et al. |
| 2010/0015184 | A1 | 1/2010 | Tuel |
| 2010/0222334 | A1 | 9/2010 | Talamonti et al. |
| 2012/0004303 | A1 | 1/2012 | Benson et al. |
| 2013/0072677 | A1 | 3/2013 | Takashima et al. |
| 2013/0079311 | A1 | 3/2013 | Muni |
| 2013/0204430 | A1 | 8/2013 | Davey et al. |
| 2014/0187628 | A1* | 7/2014 | Radke ................ A61K 47/26 514/567 |
| 2014/0371242 | A1 | 12/2014 | Wang |
| 2016/0122315 | A1 | 5/2016 | Pipal et al. |
| 2017/0065671 | A1 | 3/2017 | Maher |
| 2017/0119660 | A1 | 5/2017 | Temtsin-Krayz et al. |
| 2018/0071390 | A1 | 3/2018 | Patel et al. |
| 2019/0000862 | A1 | 1/2019 | Gizurarson |

FOREIGN PATENT DOCUMENTS

| CA | 3036356 A1 | 3/2018 |
| CN | 1756541 A | 4/2006 |
| CN | 101607086 A | 12/2009 |
| CN | 109922801 A | 6/2019 |
| EP | 1158959 B1 | 12/2011 |
| EP | 2861216 B1 | 4/2019 |
| EP | 3509592 A1 | 7/2019 |
| WO | WO-0103707 A1 | 1/2001 |
| WO | WO-2006018814 A2 | 2/2006 |
| WO | WO-2018049184 A1 | 3/2018 |

OTHER PUBLICATIONS

Extended European Search Report for EP Appl. No. 17814171.9 dated Jan. 2, 2020.
Final Office Action dated Jun. 24, 2020, for U.S. Appl. No. 16/331,733.
FIRST®—Metronidazole 50. Metronidazole 50 mg/ml, in FIRST®—Grape II Suspension Compounding Kit. [retrieved from internet Dec. 21, 2017] URL:http://cutispharma.com/wp-content/uploads/2016/11/PI Metronidazole-50 RevO.pdf Issued Sep. 2016.
Flagyl Suspension Patient Package Insert [retrieved from internet on Dec. 21, 2017] URL: https://www.old.health.gov.il/units/pharmacy/trufot/alonim/Flagy_suspension_SH_180813_eng_1441616683385.pdf, published 2013, Active ingredient and its concentration, further information.

(Continued)

*Primary Examiner* — Sin J Lee
(74) *Attorney, Agent, or Firm* — Wilson Sonsini Goodrich & Rosati

(57) ABSTRACT

Suspensions of metronidazole or baclofen and/or salts or ester derivative thereof, such as metronidazole benzoate, are disclosed. The suspension my include metronidazole or baclofen, and/or a salt or ester derivative thereof a hydrocolloid stabilizer, simethicone emulsion, a buffer, such as sodium citrate, (dihydrate), a preservative, a thickening agent, a sweetener, and water.

9 Claims, No Drawings

(56) References Cited

OTHER PUBLICATIONS

Hoelgaard and Moller, Hydrate formation of metronidazole benzoate in aqueous suspensions, International Journal of Pharmaceutics, vol. 15(2), Jun. 1983, pp. 213-221.

International Search Report for PCT/US2017/050714 dated Jan. 2, 2018.

Metronidazole for bacterial infections—a product information leaflet with a publication date of Apr. 5, 2012, obtained from the website https://www.nnedicinesforchildren.org.uk/nnetronidazole-bacterial-infections.

Non-Final Office Action dated Oct. 18, 2019 for U.S. Appl. No. 16/331,733.

Process for Preparing Posaconazole oral suspension, IP.Com Journal, IP.com, Inc. West Henrietta, NY US May 8, 2013, XP013157146, ISSN: 1533-0001.

Product Information Flagyl S Suspension® [retrieved from internet Dec. 21, 2017] URL:http://products.sanofi.com.au/auspi flagylS.pdf published Nov. 18, 2013.

Rosemont® Package Leaflet: Information for the User Norzol® 200mg/5ml Oral Suspension Metronidazole Benzoate [retrieved from internet Dec. 21, 2017] URL:https://www.drugs.com/uk/pdfleaflet/903553.pdf published Feb. 2015, Contents of the pack and other information.

Zietsman, Sharon Lynne, Dissertation: An Investigation into the Development of a Stable Aqueous Suspension of Metronidazole Benzoate for Oral Use, submitted in fulfilment of the requirements for the degree of Magister Scientiae in the Faculty of Health Sciences at the Nelson Mandela Metropolitan University, Dec. 2005, South Africa, pp. 227-274.

"Allen, Loyd V, et al., "Stability of ketoconazole, metolazone, metronidazole, procainamide hydrochloride, and sphronolactone in extemporaneously compounded oral liquids" Am j Health-Syst Pharm, vol. 53, pp. 2073-2078".

* cited by examiner

SUSPENSIONS AND DILUENTS FOR METRONIDAZOLE AND BACLOFEN

RELATED APPLICATIONS

This application is a continuation of U.S. application Ser. No. 16/331,733, filed on Mar. 8, 2019, which is a national stage filing under 35 U.S.C. 371 of International Patent Application No. PCT/2017/050714, filed Sep. 8, 2017, which claims benefit of U.S. Provisional No. 62/385,325 filed Sep. 9, 2016, each of which is hereby incorporated by reference in its entirety.

BACKGROUND OF THE INVENTION

Medications are often prescribed in a solid dosage form which many patients are unable to swallow, requiring these medications to be administered in an oral liquid form. The populations unable to swallow solid dosage forms and are in need of liquid formulations include pediatric patients, older patients with dysphagia, ICU patients and patients on enteral nutrition.

SUMMARY OF THE INVENTION

Disclosed herein are suspensions of metronidazole or baclofen and/or salts thereof. The suspensions may comprise metronidazole or baclofen or a salt thereof, such as metronidazole benzoate, a hydrocolloid stabilizer, simethicone emulsion, sodium citrate, (dihydrate), a preservative, a thickening agent, a sweetener, and water. In some embodiments, the suspension comprises metronidazole or baclofen. In some embodiments, the hydrocolloid stabilizer is microcrystalline cellulose and/or carboxymethylcellulose sodium. In one embodiment, the hydrocolloid stabilizer is Avicel RC591. In some embodiments, the thickening agent is xanthan gum.

A variety of sweeteners and flavorings can be used to improve palatability of the disclosed formulations. In some embodiments, the sweetener is one or more of ammonium glycyrrhizate, sucralose, and saccharin sodium. In some embodiments, the formulation comprises flavor grape 59.266/A. In some embodiments, the preservative is sodium benzoate and/or citric acid.

In some aspects of the invention, the pH of the formulation is between 3.6 and 4.6. In other aspects of the invention, the pH of the formulation is 3.4 and 4.0, 3.0-4.0, 3.0-5.0, or 3.0-6.0. In some embodiments, the formulation retains homogeneity of less than +/−5% of assay for active pharmaceutical ingredient after at least 30 days, at least 40 days, at least 45 days, at least 60 days, at least 75 days, at least 100 days, each up to alterntatively 100 days, 200 days, 1 year or two years. In other embodiments, the formulation retains homogeneity of less than +/−10% of assay for active pharmaceutical ingredient after at least 30 days, at least 40 days, at least 45 days, at least 60 days, at least 75 days, at least 100 days, each up to alterntatively 100 days, 200 days, 1 year or two years. In some embodiments the homogeneity is assessed for samples stored at room temperature.

One embodiment of the liquid formulations as taught by the invention comprises ammonium glycyrrhizate (magnasweet 100), Avicel RC591, citric acid (anhydrous), grape flavor, saccharin sodium, simethicone emulsion, sodium benzoate, sodium citrate, sucralose, xanthan gum, and water.

In a specific embodiment a liquid formulation of the invention comprises:
a. 0.05000% (w/v) ammonium glycyrrhizate, (magnasweet 100);
b. 1.500% (w/v) Avicel RC591;
c. 0.500% (w/v) citric acid, (anhydrous);
d. 0.0500% (w/v) flavor grape 59.266/A;
e. 0.0300% (w/v) saccharin sodium;
f. 0.2000% (w/v) simethicone emulsion, (30%);
g. 0.1500% (w/v) sodium benzoate;
h. 0.2000% (w/v) sodium citrate, (dihydrate);
i. 0.1000% (w/v) sucralose;
j. 0.1000% (w/v) xanthan gum;
k. purified water.

Another embodiment of the liquid formulations as taught by the invention comprises citric acid, D&C Yellow No. 10, FD&C Red No 40, grape flavor, hydroxyethyl cellulose, propylene glycol, simethicone emulsion, sodium benzoate, sucralose, and water.

In a specific embodiment a liquid formulation of the invention comprises:
a. 0.12% (w/v) citric acid, (anhydrous);
b. 0.0002% (w/v) D&C Yellow No. 10;
c. 0.000038% (w/v) FD&C Red No. 40;
d. 0.0500% (w/v) flavor grape 59.266/A;
e. 0.5000% (wv) hydroxyethyl cellulose;
f. 5.000% (w/v) propylene glycol;
g. 0.1500% (w/v) simethicone emulsion, (30%);
h. 0.1000% (w/v) sodium benzoate;
i. 0.2000% (w/v) sucralose;
j. purified water.

In some embodiments a liquid formulation of the invention comprises 0.12-0.6% (w/v) citric acid; 0.1500-0.250% (w/v) simethicone emulsion; 0.1000-0.1550% (w/v) sodium benzoate; sweetener and water.

Disclosed herein are diluents for reconstituting metronidazole or baclofen or a salt thereof. In some embodiments, the liquid diluent comprises 0.03-0.08% (w/v) ammonium glycyrrhizate; 1.0-2.0% (w/v) Avicel RC591; 0.1-0.9% (w/v) citric acid; 0.01-0.10% (w/v) flavoring; 0.01-0.05% (w/v) saccharin sodium; 0.1-0.3% (w/v) simethicone emulsion; 0.1-0.2% (w/v) sodium benzoate; 0.1-0.3% (w/v) sodium citrate, (dihydrate); 0.05-0.2% (w/v) sucralose; 0.05-0.2% (w/v) xanthan gum; and purified water.

In a specific embodiment, the liquid diluent comprises 0.05% (w/v) ammonium glycyrrhizate, (magnasweet 100); 1.50% (w/v) Avicel RC591; 0.50% (w/v) citric acid, (anhydrous); 0.05% (w/v) flavor grape 59.266/A; 0.03% (w/v) saccharin sodium; 0.2% (w/v) simethicone emulsion, (30%); 0.15% (w/v) sodium benzoate; 0.20% (w/v) sodium citrate, (dihydrate); 0.10% (w/v) sucralose; 0.10% (w/v) xanthan gum; and purified water.

Further disclosed herein are suspensions of metronidazole or baclofen or a salt thereof, comprising metronidazole or baclofen or a salt of metronidazole or baclofen; simethicone emulsion; sodium bicarbonate; and sodium citrate, (dihydrate), where the suspension is stable for at least 30 days when stored at 2-8 or 15-30 degrees celsius. In some embodiments, the suspension is stable for at least 30 days when stored at 38-42 degrees celsius. In some embodiments, the suspension comprises a pH of no more than pH 4.6, 5.5, or 6.5. In some embodiments, the suspension comprises a pH of 4.

In some embodiments, the formulations described herein retain homogeneity of less than +/−2%, +/−5%, or +/−10% of assay for active pharmaceutical ingredient after at least 30 days, 60 days or 90 days. In some embodiments, the formulations described herein maintain homogeneity of the active pharmaceutical ingredient at room temperature for at least 30 days, at least 40 days, at least 45 days, at least 60 days, at least 75 days, at least 100 days, each up to alternatively 100 days, 200 days, 1 year or two years after reconstitution. In some embodiments the formulations described herein maintain homogeneity of the active pharmaceutical ingredient for 30 days-two years 40 days-two years, 90 days-two years, 1-2 years, 1½ years-2 years or up to 2 years.

In any of the metronidazole suspensions described herein the suspension may be prepared with micronized metronidazole.

In some aspects the invention is a suspension of baclofen or a salt thereof, that includes baclofen or a salt thereof; a hydrocolloid stabilizer, simethicone emulsion; sodium citrate, (dihydrate); a preservative, a thickening agent, a sweetener, and water. In some embodiments the hydrocolloid stabilizer is microcrystalline cellulose and/or carboxymethylcellulose sodium. In other embodiments the thickening agent is xanthan gum. In other embodiments the pH of the formulation is between 3.6 and 4.6. In yet other embodiments the formulation retains homogeneity of less than +/−5% or less than +/−10% or any percentage there between of assay for active pharmaceutical ingredient after at least 30 days.

In a specific embodiment a liquid formulation of the invention comprises baclofen plus:
- 0.05000% (w/v) ammonium glycyrrhizate, (magnasweet 100);
- 1.500% (w/v) Avicel RC591;
- 0.500% (w/v) citric acid, (anhydrous);
- 0.0500% (w/v) flavor grape 59.266/A;
- 0.0300% (w/v) saccharin sodium;
- 0.2000% (w/v) simethicone emulsion, (30%);
- 0.1500% (w/v) sodium benzoate;
- 0.2000% (w/v) sodium citrate, (dihydrate);
- 0.1000% (w/v) sucralose;
- 0.1000% (w/v) xanthan gum;
- purified water.

A suspension of baclofen, comprising a salt of baclofen; simethicone emulsion; sodium bicarbonate; and sodium citrate, (dihydrate), wherein the suspension is stable for at least 30 days when stored at 2-8 degrees celsius is provided in other aspects of the invention.

In some embodiments the suspension comprises a pH of no more than pH 4.6. In other embodiments the formulation retains homogeneity of less than +/−5% of assay for active pharmaceutical ingredient after at least 60 days.

Each of the embodiments of the invention can encompass various recitations made herein. It is, therefore, anticipated that each of the recitations of the invention involving any one element or combinations of elements can, optionally, be included in each aspect of the invention.

DETAILED DESCRIPTION

The invention encompasses liquid compounded formulations of metronidazole or baclofen and salts or ester derivatives thereof such as metronidazole benzoate, diluents that can be used by a pharmacist to reconstitute metronidazole or baclofen or a salt or ester derivative thereof, and related compounding kits. In some embodiments, the invention encompasses liquid compounded formulations of metronidazole or baclofen, diluents that can be used by a pharmacist to reconstitute metronidazole or baclofen, and related compounding kits.

Commonly, pediatric and geriatric populations encounter difficulty being administered solid oral dosage forms such as capsules and tablets which may lead to noncompliance with the recommended pharmacotherapy with the solid oral dosage forms and likely results in rendering the therapy ineffective. Solid oral dosage forms are usually not favorable for pediatric and geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released.

For most community pharmacies (retail/chain and independent), compendial metronidazole oral formulations do not provide ease of use, flavoring, flexible dosing, or a uniform formulation. Commercially available dosage forms include many gels, lotions, tablets, capsules, and solutions for injections, including 170 marketing authorizations currently recognized in the United States by the U.S. National Library of Medicine, DailyMed listing, however none of these are liquids for oral dosing.

The liquid formulations of the invention is stable for at least 30 days, at least 40 days, at least 45 days, at least 60 days, at least 75 days, at least 100 days, each up to alternatively 100 days, 200 days, 1 year, or two years or for 30 days-two years 40 days-two years, 90 days-two years, 1-2 years, 1½ years-2 years or up to 2 years under room temperature storage conditions. The liquid formulations of the invention have improved palatability compared to the compendial formulation, and when compared to previously described oral formulations or compounded formulations. The liquid formulations disclosed herein have improved homogeneity when compared to commercially available liquid formulations.

Metronidazole is an antibiotic and antiprotozoal drug with a broad range of indications, many of which require or benefit from oral dosing, including bone and joint infections, endocarditis, various gynecologic infections, intra-abdominal infections, meningitis, and other CNS infections, infections of the respiratory tract, septicemia, infections of the skin and skin structure, amebiasis, bacterial vaginosis, Balantiadiasis, *Blastocystis hominis* infection, *Clostridium difficile*-associated diarrhea (CDAD) and associated conditions, Crohn's Disease, including refractory perianal Crohn's Disease, infection by *Dientameoba fragilis*, infection by *Dracunculus medinensis* (Guinea Worm), giardiasis, *Helicobacter pylori* infection and associated duodenal ulcer disease, non-gonococcal urethritis, pelvic inflammatory disease, Rosacea, infection by Clostridial bacteria, especially *C. tetani*, and trichomoniasis.

In addition, metronidazole can be used as perioperative prophylaxis where there is a risk of anaerobic bacterial infection, for example in colorectal surgery or appendectomy. Furthermore, metronidazole is used as a component of anti-infective, post-exposure prophylaxis in sexual assault victims. In many of these conditions, patients may, as a result of the conditions, or as a result of comorbidities, have difficulty in taking drug, or be unwilling or unable to take drug in tablet or capsule presentations. The disclosed liquid formulations provide clinicians and patients with convenient and palatable alternative dosing formats that allow precise adjustment of dose, and enhance patient compliance with clinician orders.

In specific patient populations, such as those with hepatic impairment, a clinician may need to adjust the dose of metronidazole and monitor serum concentrations to balance therapeutic benefit against risk in subjects with reduced liver function. The liquid formulations disclosed herein provide clinicians with a tool to make fine adjustments to oral dosing is such patients. Similarly, in geriatric patients, the age-related changes in the pharmacokinetics of metronidazole can require clinicians to adjust dosage. The liquid formulations disclosed herein provide clinicians with a tool to make fine adjustments to oral dosing is such patients in order to maximize therapeutic benefit while managing patient risk in a way that cannot be efficiently achieved by dosing with fractional tablets or capsules.

Baclofen (β-(4-chlorophenyl)-GABA) is a muscle relaxer and an antispastic agent that is often used to treat muscle symptoms caused by multiple sclerosis, including spasm, pain, and stiffness. Baclofen acts on the central nervous system to relieve spasms, cramping, and tightness of muscles caused by spasticity. It is a GABA receptor agonist (derivative of γ-aminobutyric acid (GABA)) that acts specifically on the GABA-B receptors. Baclofen is beleived to block mono-and-polysynaptic reflexes by acting as an inhibitory neurotransmitter, blocking the release of excitatory transmitters.

The liquid formulations disclosed herein maintain stability and homogeneity for at least thirty days. With respect to stability, samples of the disclosed formulations show greater than 90%, or greater than 95%, or greater than 97.5% of the nominal concentration or starting concentration of metronidazole when measured in an assay compliant with the assay for Metronidazole benzoate, thirty days after the liquid is formulated. Alternately, when assayed thirty days after the liquid is formulated, samples average to greater than 90%, or greater than 95%, or greater than 97.5%, or greater than 98%, or greater than 99% of the nominal concentration or starting concentration of metronidazole or baclofen. With respect to homogeneity, samples of the disclosed formulations taken from the top, middle, and bottom of the container of formulated drug show greater than 90%, or greater than 95%, or greater than 97.5% of the nominal concentration or starting concentration of metronidazole, when measured in an assay compliant with the assay for metronidazole or baclofen thirty days after the liquid is formulated. Alternately, when assayed thirty days after the liquid is formulated, samples taken from the top, middle, and bottom of the container of formulated drug show less than 10%, less than 5%, less than 2%, less than 1% or less than 1% but greater than 0.5% variation from each other, or from the average concentration measured thirty days after formulation or from the nominal concentration of metronidazole or baclofen.

An advantage of the invention is the flexibility of dose that can be prescribed by the physician. The ability to reconstitute metronidazole or baclofen or a salt or ester derivative thereof, in a liquid formulation to be dosed orally to a patient later in the day, over the course of several days, over the course of a week, or over the course of several weeks, provides ease of use to the compounding pharmacist, physician, and patient. This provides a time saving and cost effective method of producing multiple drug doses in the pharmacy for a single patient. In addition, as the method described utilized bulk API rather than recycling final dosage forms of licensed drug products (i.e. recovering granules of drug from drug capsules) the invention provides additional consistency over alternative compounding formulation methods. In some embodiments, the formulations described and the preparation methods disclosed produce comparably stable and homogenous liquid formulations from more than one source of bulk API, demonstrating the broad applicability of the methods disclosed.

The ability to use the liquid formulations of the invention also offers advantages to physicians, as it provides the ability to prescribe with more flexibility for a range of challenging and otherwise vulnerable patients. The palatability of the disclosed formulations improves patient compliance and minimizes patient distress. The liquid nature of the formulations disclosed allows the dosing of metronidazole or baclofen and salts or ester derivatives thereof, to children who are unable to reliably swallow capsules.

In addition, the liquid nature of the formulations disclosed allows the dosing of metronidazole or baclofen and salts or ester derivatives thereof, to elderly patients who are unable to reliably swallow capsules. Furthermore, the liquid nature of the formulations disclosed allows the dosing of metronidazole or baclofen to critical care patients who are otherwise unable to swallow capsules due to intubation or other injuries, pathologies, or interventions that inhibit the ability to receive or take medication in solid format.

The liquid formulations disclosed provide a vehicle for the delivery of a suspension of metronidazole or baclofen or salts or ester derivatives thereof, within a diluent comprising microcrystalline cellulose, simethicone emulsion, a buffer system (for example sodium bicarbonate and/or sodium citrate), one or more preservatives, one or more thickening agents, one or more sweeteners and/or flavorings, and water. While not excluding the possibility that other ingredients contribute to the stability of the formulation, microcrystalline cellulose and/or carboxymethycellulose sodium are included to stabilize the active ingredient. Similarly, the use of simethecone contributes to stability by minimizing the formation of foam on mixing or agitation during formulation, or incidentally during transport, use, and storage. The formation of foam could be associated with conditions denaturing the API or conditions that would diminish the patient's ability to measure an exact dose, sodium bicarbonate and/or sodium citrate can be used to provide a buffered diluent that promotes the maintenance of a constant pH during liquid storage after formulation. Thickening agents and sweeteners are included to improve the handling, appearance, and palatability of the finished dosage.

Other buffers that can be used in the suspensions and diluents described herein include pharmacologically acceptable combinations of cations selected from sodium, potassium, magnesium, calcium, and aluminum and anions selected from bicarbonate, hydroxide, gluconate, glycinate, and other appropriate amino acid salts. Additional buffering agents can include other forms of citrate, tartrates, acetates, carbonates, phosphates, metaphosphates, glycerophosphates, polyphosphates, pyrophosphates, and certain oxides in pharmacologically and pharmaceutically acceptable combinations of anions and cations providing buffering capacity as known in the art.

Preservatives that can be used in the formulations disclosed herein include anti-microbials, anti-oxidants, and agents providing biocidal or biostatic activity, such that a low bioburden is maintained in the formulation of the invention from preparation through storage, and during routine use by patients and clinicians. Exemplary preservatives include benzyl alcohol or other pharmaceutically acceptable alcohol, ascorbic acid, ascrobyl palmitate or other pharmaceutically acceptable ascorbate salts, BHA, BHT, citric acid or other citrate salts, sodium benzoate, benzoic acid or other pharmaceutically acceptable benzoate salts, sodium bisulfate, sodium metabisulfite, sodium sulfite, parabens, potassium sorbate or other pharmaceutically acceptable sorbate salts, or vanillin.

Sweeteners or sweetening agents may include any compounds that provide a sweet taste to enhance the palatability of the formulation, including natural and synthetic sugars and natural and synthetic sweeteners (i.e., non-sugar sweetening agents). These could include glucose, fructose, sucrose, or other pharmaceutically acceptable monosaccharide and disaccharides or sugar alcohols, such as xylitol. Also, sweeteners may include maltodextrin, polydextrose and the like. Other sweeteners may include glycerin, inulin, maltol, salts of acesulfame, alitame, aspartame, neotame, cyclamate salts, saccharin and its salts, and other artificial and naturally-occurring agents providing sweetness either singly or in combination.

In other embodiments, the liquid formulations comprise a flavoring agent or flavorant to enhance the flavor or aroma of the dose, and to improve general palatability of the dose, thus helping to mask the flavor of the metronidazole or baclofen, or salt or ester derivative thereof, active ingredient which patients may find unpleasant. This provides an improved experience for patients, and better compliance with the drug regimen desired by clinicians. Suitable natural or artificial flavors can be selected from pharmaceutically acceptable options as described in standard pharmacy references which are known to those skilled in the art. In a particular embodiment, grape flavor is used. The use of grape flavor has been found to be effective in helping to mask the unpleasant flavor of metronidazole or baclofen and salts or ester derivatives thereof. Natural and synthetic flavors can be used and adapted to the palate of diverse patient populations, including but not limited to, age- and culturally-related flavor preferences (for example bubble gum flavor for pediatric patients).

In further embodiments, the liquid formulation may contain a pharmaceutically acceptable coloring agent. Many such agents are approved for use by the U.S. Food and Drug Administration, and are well known to those skilled in the art of compounding pharmacy. The use of color can enhance the aesthetic appearance of the dose as well as providing confirmation of the identity of the drug in a context where more than one oral formulation is being prepared, stored, transported, or used. Enhancing the aesthetic appearance of the dose increased the overall palatability of the dose, which provides benefits to patients and clinicians in terms of improved patient experience and improved compliance with the drug regimen. The ability to unambiguously identify the medication in the pharmacy, clinical, and patient context provides benefits to the patient by reducing the scope for errors in the preparation, storage, handling, transport, and use of the medication. In addition, the use of color in the formulations can mask color changes in the formulation lacking additional color agents. For example, uncolored formulations may change color due to chemical changes taking place during storage that do not affect the safety, potency, or efficacy of the medication, but that might confuse a patient or clinician, or that might lead to a lack of compliance with a prescribed drug regimen.

A key problem in devising oral liquid formulations that are practical, safe, and effective to make and use, is the balance required between palatability and the handling requirements of the dose form on the one hand, and the stability of the formulation and the homogeneity of the doses on the other. Where, as in the present invention, it is desired to produce a liquid medication for oral delivery in a series of doses spread over time, it is critical to provide a formulation in which the potency of the API remains acceptably constant over the time that the formulation is to be used, so that from the first dose to last dose, the same dose of active drug is delivered per unit volume of the formulation dosed to the patient. In addition, as in the case of the present invention where the API is presented as a suspension in a liquid formulation, it is necessary that the formulation is capable of providing homogenous doses. That is, that the API does not clump, settle to the bottom, float to the top, or stick to the sides of the container or any dosing or manufacturing device in a manner that would cause the dose of API contained in unit volume doses obtained from the preparation to vary unacceptably. It is generally desirable for the formulation to be sufficiently pleasant for the patient to consume and assure compliance with the regimen prescribed by the clinician, where the dose is delivered orally. It is generally desirable for the viscosity of the liquid formulation to be low enough to facilitate handling of the formulation in the manufacture, storage, and dosing in a manner such that there are not unacceptable losses of drug, i.e., material adhering to the containers or equipment used for manufacture and storage or by adherence or clumping within the drug delivery device such as a nasogastric feeding tube. If too much drug adheres to and clumps on equipment and containers used to make, store, and deliver doses, then the delivery of API to the patient becomes unreliable, which undermines the consistency, efficacy, and safety of therapy.

Specific examples are provided below of pharmaceutically acceptable formulations that achieve appropriate homogeneity and stability in useful, practical, and palatable presentations.

Unless defined otherwise, all technical and scientific terms used herein have the same meanings as commonly understood by one skilled in the art. Although any methods and materials similar or equivalent to those described herein can be used in the practice of testing of embodiments described herein, certain preferred methods, devices, and materials are now described.

As used herein, active pharmaceutical ingredient (or "API") refers to metronidazole or baclofen and/or a salt or ester derivative thereof, for example, metronidazole benzoate.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having,"

"includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent is a bactericide, amebicide or trichomonacide. In some embodiments the therapeutic agent direct anti-inflammatory effects, effects on neutrophil motility, effect on lymphocyte transformation, and effects on cell-mediated immune function. In some embodiments the therapeutic agent is bactericidal or bacteriostatic against gram positive anaerobes and gram negative anaerobes. In some embodiments the therapeutic agent is active against *Helicobacter pylori, Entamoeba hystolytica, Trichomonas vaginalis, Giardia lambalia,* or *Balantidium coli.*

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is a child. In certain instances, the human is elderly. Other examples of subjects include experimental animals such as mice, rats, dogs, cats, goats, sheep, pigs, and cows.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation of gastric acid secretion.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Various aspects of the embodiments described above may be used alone, in combination, or in a variety of arrangements not specifically discussed in the embodiments described in the foregoing, and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

An exemplary formulation of a liquid diluent of the present invention was prepared. In order to make a relative high viscosity formulation with approximately 255 cP viscosity in a preparation at batch size of 2 liters, the following method was successfully used. For reference purposes, this formulation is referenced herein as Formula 6 in some embodiments.

1. 1700 mL of purified water, was added to a suitable container.
2. 30.0 grams of Avicel RC-591 was added while mixing the preparation.

3. 2.00 grams of xanthan gum, was added to the preparation while continuing to mix.
4. The preparation was mixed for 30 to 60 minutes.
5. 1.00 grams of ammonium glycyrrhizate, (also known as magnasweet 100) was added to preparation while continuing to mix.
6. 0.600 grams of saccharin sodium, was added to the preparation while continuing to mix.
7. 4.00 grams of sodium citrate, (dihydrate) was added to the preparation while continuing to mix.
8. 3.00 grams of sodium benzoate, was added to the preparation while continuing to mix.
9. 2.00 grams of sucralose, was added to the preparation while continuing to mix.
10. Mixing was continued for 10 to 20 minutes.
11. 10.0 grams of citric acid, (anhydrous) was added to the preparation while continuing to mix.
12. 4.00 grams of simethicone emulsion, (30%) was added to the preparation while continuing to mix.
13. 1.00 grams of flavor grape 59.266/A was added to the preparation while continuing to mix.
14. Mixing was continued for 10 to 20 minutes.
15. The mixing was stopped and sufficient purified water, was added to make the final volume up to 2000 mL.
16. The diluent was mixed for a further 10-15 minutes.
17. The batch was transferred to containers using bottle B325-38-BLA-WHT and cap 8040-A.

Properties of the diluent, an off-white liquid with a grape odor, were determined. The dynamic viscosity (30 RPM at 25° C.) was found to be 255 cP, the density was found to be 1.01 g/mL, and the pH was 3.72 at 25.1° C.

Example 2

Physicochemical properties and data characterizing the stability and homogeneity of metronidazole formulated to 50 mg/ml and 100 mg/mL in the liquid diluent described above as Formula 6 were determined. Suspensions produced with micronized versus non-micronized metronidazole were compared. The metronidazole suspension was prepared using a suspension kit at 40° C. and 75% RH. The suspension was then stored at 25° C. and 60% RH for an extended period of time. Samples were tested for stability after 15 and 30 days of storage. The concentration of the API (metronidazole benzoate) in samples obtained from the top, middle (meaning midway between the surface of the liquid and the bottom of the container) and bottom of the container containing the formulated drug were measured. The metronidazole assay was run on a HPLC with samples of 5.00 μL for 18 minutes. The data for the 50 mg/ml suspension produced from micronized metronidazole is shown in Table 1 and the data for the 100 mg/mL suspension produced from micronized metronidazole is shown in Table 2.

TABLE 1

| | | | Time Point: Kits | | | | | |
|---|---|---|---|---|---|---|---|---|
| | | | Initial | Initial | Initial | Initial | Initial | 3 M |
| | | | Pull Date: Kits for Compounding | | | | | |
| | | | N/A | N/A | N/A | N/A | N/A | |
| | | | Time Point: Compounded Solution (in-use) | | | | | |
| Testing | Method | Specification | Initial | 15 days | 30 days | 60 days | 90 days | Initial |
| Appearance of Suspension | ATM-1095 | A slightly hazy, white to slightly yellow liquid with a grape odor | A slightly hazy, slightly yellow liquid with a grape odor | A slightly hazy, slightly yellow liquid with a grape odor | A slightly hazy, slightly yellow liquid with a grape odor | | | |
| pH | USP<791> | Report Results | 3.7 | 3.7 | 3.7 | | | |
| Assay | USP | 90.0%-110.0% of label claim | Top: 97.9% Middle: 98.2% Bottom: 98.1% | 97.9% | Top: 97.2% Middle: 97.4% Bottom: 97.1% | | | |

TABLE 2

| | | | Time Point: Kits | | | | | |
|---|---|---|---|---|---|---|---|---|
| | | | Initial | Initial | Initial | Initial | Initial | 3 M |
| | | | Pull Date: Kits for Compounding | | | | | |
| | | | N/A | N/A | N/A | N/A | N/A | |
| | | | Time Point: Compounded Solution (in-use) | | | | | |
| Testing | Method | Specification | Initial | 15 days | 30 days | 60 days | 90 days | Initial |
| Appearance of Suspension | ATM-1095 | A slightly hazy, white to yellow liquid with a grape odor | A slightly hazy, slightly yellow liquid with a grape odor | A slightly hazy yellow liquid with a grape odor | A slightly hazy, slightly yellow liquid with a grape odor | | | |

TABLE 2-continued

|  |  |  | Time Point: Kits | | | | | |
|---|---|---|---|---|---|---|---|---|
|  |  |  | Initial | Initial | Initial | Initial | Initial | 3 M |
|  |  |  | Pull Date: Kits for Compounding | | | | | |
|  |  |  | N/A | N/A | N/A | N/A | N/A | |
|  |  |  | Time Point: Compounded Solution (in-use) | | | | | |
| Testing | Method | Specification | Initial | 15 days | 30 days | 60 days | 90 days | Initial |
| pH | USP<791> | Report Results | 3.7 | 3.7 | 3.7 | | | |
| Assay | USP | 90.0%-110.0% of label claim | Top: 95.2% Middle: 95.3% Bottom: 94.9% | 95.5% | Top: 94.3% Middle: 95.5% Bottom: 94.5% | | | |

In contrast to the micronized metronidazole the data for a 50 mg/ml suspension produced from non-micronized metronidazole is shown below. The non-micronized metronidazole benzoate still shows a gradient from the top to the bottom. The suspensions were stored at 25±2° C./60±5% RH.

| Metronidazole Benzoate Suspension Assay Results using non-micronized metronidazole | | | | |
|---|---|---|---|---|
| Time Point | Sample | Assay | Average | RSD |
| Initial | Top Middle Bottom | 99.6% 113.3% 116.9% | 109.9% | 8.3% |

Example 3

Physicochemical properties and data characterizing the stability and homogeneity of baclofen formulated to 1 mg/ml and 5 mg/mL in the liquid diluent described above as Formula 6 were determined. Suspensions were produced at a 2 oz or 4 oz sample size using several baclofen batches and the relative stability with storage time was compared. The baclofen suspension was prepared using a suspension kit at 40° C. and 75% RH. The suspension was then stored at 25° C. and 60% RH for an extended period of time. Samples were tested for stability after 15, 30, and 60 days of storage. The concentration of the API in samples obtained from the top, middle (meaning midway between the surface of the liquid and the bottom of the container) and bottom of the container containing the formulated drug were measured. The baclofen assay was run on a HPLC with samples of 5.00 µL for 18 minutes. The data for the 1 mg/ml suspension produced in a 4 oz sample using different batches of baclofen is shown in Tables 3 and 4 respectively and the data for the 5 mg/mL suspension produced in a 4 oz or 2 oz sample is shown in Tables 5 and 6 respectively.

TABLE 3

|  |  |  | Time Point: Kits | | | | |
|---|---|---|---|---|---|---|---|
|  |  |  | Initial | | | | 3 M |
|  |  |  | Pull Date: Kits for Compounding | | | | |
|  |  |  | N/A | N/A | N/A | N/A | |
|  |  |  | Time Point: Compounded Solution (in-use) | | | | |
| Testing | Method | Specification | Initial | 15 days | 30 days | 60 days | Initial |
| Appearance of Suspension | ATM-1095 | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor |
| Assay | USP | 90.0%-110.0% of label claim | Top: 96.7% Middle: 97.0% Bottom: 96.7% | 97.4% | Top: 97.2% Middle: 96.8% Bottom: 96.8% | 97.2% | |
| pH | USP<791> | Report results | N/A | 3.8 | 3.8 | 3.8 | |

TABLE 4

| Testing | Method | Specification | Time Point: Kits | | | | |
|---|---|---|---|---|---|---|---|
| | | | Initial | Initial | Initial | Initial | 3 M |
| | | | Pull Date: kits for Compounding | | | | |
| | | | N/A | N/A | N/A | N/A | |
| | | | Time Point: Compounded Solution (in-use) | | | | |
| | | | Initial | 15 days | 30 days | 60 days | Initial |
| Appearance of Suspension | ATM-1095 | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor |
| Assay | USP | 90.0%-110.0% of label claim | Top: 95.9% Middle: 96.5% Bottom: 96.6% | 97.3% | Top: 97.1% Middle: 96.7% Bottom: 95.8% | 97.6% | |
| pH | USP<791> | Report results | N/A | 3.8 | 3.8 | 3.8 | |

TABLE 5

| Testing | Method | Specification | Time Point: Kits | | | | |
|---|---|---|---|---|---|---|---|
| | | | Initial | Initial | Initial | Initial | 3 M |
| | | | Pull Date: Kits for Compounding | | | | |
| | | | N/A | N/A | N/A | N/A | |
| | | | Time Point: Compounded Solution (in-use) | | | | |
| | | | Initial | 15 days | 30 days | 60 days | Initial |
| Appearance of Suspension | ATM-1095 | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor |
| Assay | USP | 90.0%-110.0% of label claim | Top: 101.7% Middle: 102.5% Bottom: 100.9% | 100.9% | Top: 101.1% Middle: 100.7% Bottom: 103.8% | 101.7% | |
| pH | USP<791> | Report results | N/A | 4.0 | 4.0 | 4.0 | |

TABLE 6

| Testing | Method | Specification | Time Point: Kits | | | | |
|---|---|---|---|---|---|---|---|
| | | | Initial | Initial | Initial | Initial | 3 M |
| | | | Pull Date: Kits for Compounding | | | | |
| | | | N/A | N/A | N/A | N/A | |
| | | | Time Point: Compounded Solution (in-use) | | | | |
| | | | Initial | 15 days | 30 days | 60 days | Initial |
| Appearance of Suspension | ATM-1095 | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor | A slightly hazy, white liquid with a grape odor |
| Assay | USP | 90.0%-110.0% of label claim | Top: 98.0% Middle: 98.3% Bottom: 96.8% | 96.8% | Top: 97.0% Middle: 97.1% Bottom: 97.1% | 96.9% | |
| pH | USP<791> | Report results | N/A | 4.0 | 4.0 | 4.0 | |

The diluent of the invention produced highly superior stability of the metronidazole and baclofen suspensions.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

Example 4

An exemplary liquid formulation present invention was prepared. For reference purposes, this formulation is referenced herein as Formula R9990, in some embodiments. Methods for preparing the formulation can be found below:

1. 5 L of colorant solution was prepared in a suitable container.
2. 400.0 grams of sucralose was prepared in a suitable container.
3. 200.0 grams of sodium benzoate, was added to the preparation while continuing to mix.
4. 240.0 grams of citric acid, was added to the preparation while continuing to mix.
5. 1000.0 grams of Baclofen, was added to the preparation while continuing to mix.
6. 10000.0 grams of propylene glycol was transferred into a suitable container and 1000.0 grams of hydroxyethyl cellulose was added. The mixture was then added to the preparation while continuing to mix.
7. 300.0 grams of simethicone emulsion was added to the preparation while continuing to mix.
8. The preparation was mixed for 30 to 60 minutes.
9. The colorant solution was added to the preparation while continuing to mix.
10. 100.0 grams of flavor grape 59.266/A was added to the preparation while continuing to mix.

Physicochemical properties and data characterizing the stability of the baclofen solution 1 mg/ml and baclofen suspension 5 mg/mL using Formula R9990 above were determined. Suspensions were produced at a 4 oz or 10 oz sample size and the relative stability with storage time was compared. The stability data for the 1 mg/ml solution produced in a 10 oz sample at 38-42 degrees Celsius is shown in Tables 7 and the data for the 5 mg/mL suspension produced in a 4 oz sample at 38-42 degrees Celsius is shown in Tables 8.

TABLE 7

| Testing | Method | Specification | Time Point: Initial | 1 M |
|---|---|---|---|---|
| Appearance of Solution | Organoleptic | A slightly hazy, yellow to orange liquid with a grape odor | A slightly hazy, yellow to orange liquid with a grape odor | A slightly hazy, white liquid with a grape odor |
| Baclofen Assay | In-house | 90.0%-110.0% of label claim | 100% | 100% |
| Sodium Benzoate Assay | In-house | 80.0%-120.0% of label claim | 101% | 101% |
| pH | USP<791> | Report results | 4.0 | 4.0 |
| Density | In-house | Report results | 1.00 | 1.00 |

TABLE 8

| Testing | Method | Specification | Time Point: Initial | 1 M |
|---|---|---|---|---|
| Appearance of Solution | Organoleptic | A slightly hazy, yellow to orange liquid with a grape odor | A slightly hazy, yellow to orange liquid with a grape odor | A slightly hazy, white liquid with a grape odor |
| Baclofen Assay | In-house | 90.0%-110.0% of label claim | 101% | 102% |
| Sodium Benzoate Assay | In-house | 80.0%-120.0% of label claim | 102% | 102% |
| pH | USP<791> | Report results | 4.2 | 4.3 |
| Density | In-house | Report results | 1.00 | 1.01 |

The invention claimed is:

1. A liquid pharmaceutical composition that comprises:
 a) 5 mg/ml of baclofen or a salt thereof;
 b) 0.12% (w/v) of citric acid (anhydrous);
 c) 0.5% (w/v) of hydroxyethyl cellulose;
 d) 5% (w/v) of propylene glycol;
 e) 0.15% (w/v) of simethicone emulsion (30%);
 f) 0.1% (w/v) of sodium benzoate;
 g) 0.2% (w/v) of sucralose; and
 h) water,
wherein a pH of the pharmaceutical composition is between 3.0 and 6.0, and
wherein the pharmaceutical composition retains less than +/−5% variation of baclofen concentration measured by a USP assay for at least 30 days when stored at room temperature.

2. The pharmaceutical composition of claim 1, wherein the pharmaceutical composition further retains less than +/−5% variation of baclofen concentration measured by a USP assay for at least 30 days when stored at 38-42° C.

3. The pharmaceutical composition of claim 1, wherein the pharmaceutical composition further retains less than +/−5% variation of baclofen concentration measured by a USP assay for at least 30 days when stored at 15-30° C.

4. The pharmaceutical composition of claim 1, wherein the pharmaceutical composition further comprises a coloring agent, a flavoring agent, or a combination thereof.

5. The pharmaceutical composition of claim 1, wherein the pharmaceutical composition comprises 0.0002% (w/v) of D&C Yellow No. 10.

6. The pharmaceutical composition of claim 1, wherein the pharmaceutical composition comprises 0.000038% (w/v) of FD&C Red No. 40.

7. The pharmaceutical composition of claim 1, wherein the pharmaceutical composition comprises 0.0500% (w/v) of flavor grape 59.266/A.

8. The pharmaceutical composition of claim 1, wherein the pH of the pharmaceutical composition is about 3.6 to 4.6.

9. The pharmaceutical composition of claim 1, wherein the pH of the pharmaceutical composition is about 4.0 to 4.3.

* * * * *